US010702275B2

(12) United States Patent
Adams et al.

(10) Patent No.: US 10,702,275 B2
(45) Date of Patent: Jul. 7, 2020

(54) MEDICAL DEVICE WITH STIFFENER WIRE FOR OCCLUDING VASCULAR DEFECTS

(75) Inventors: Daniel O. Adams, Long Lake, MN (US); Ryan Kariniemi, Cokato, MN (US); Brooke Ren, Maple Grove, MN (US); Matthew C. Heidner, Maple Grove, MN (US)

(73) Assignee: St. Jude Medical Cardiology Division, Inc., St. Paul, MN (US)

( * ) Notice: Subject to any disclaimer, the term of this patent is extended or adjusted under 35 U.S.C. 154(b) by 1159 days.

(21) Appl. No.: 12/372,854

(22) Filed: Feb. 18, 2009

(65) Prior Publication Data

US 2010/0211046 A1 Aug. 19, 2010

(51) Int. Cl.
*A61B 17/12* (2006.01)
*A61B 17/00* (2006.01)
*A61M 25/00* (2006.01)

(52) U.S. Cl.
CPC .... *A61B 17/12122* (2013.01); *A61B 17/0057* (2013.01); *A61B 17/12172* (2013.01); *A61B 2017/00592* (2013.01); *A61B 2017/00597* (2013.01); *A61B 2017/00606* (2013.01); *A61B 2017/00615* (2013.01);
(Continued)

(58) Field of Classification Search
CPC .......... A61B 17/0057; A61B 17/12136; A61B 17/12109; A61B 17/12027; A61B 17/12031; A61B 17/12036; A61B 17/1204; A61B 17/12099; A61B 17/12113; A61B 2017/12022; A61B 2017/00632; A61B 2017/00646; A61B 2017/00659; A61B 2017/00637; A61B 2017/00641; A61B 17/12122; A61B 17/12172; A61B 2017/00575; A61B 2017/00592; A61B 2017/00597; A61B 2017/00606; A61B 2017/00615; A61B 2017/00867; A61F 6/146; A61F 6/20
USPC ....... 606/213, 157, 158, 191, 194, 195, 198, 606/200
See application file for complete search history.

(56) References Cited

U.S. PATENT DOCUMENTS

| 5,108,420 | A | | 4/1992 | Marks |
| 5,334,210 | A | * | 8/1994 | Gianturco ..................... 606/151 |
| 5,725,552 | A | | 3/1998 | Kotula et al. |

(Continued)

FOREIGN PATENT DOCUMENTS

| EP | 1 955 661 A2 | 8/2008 |
| EP | 2 014 239 A2 | 1/2009 |

*Primary Examiner* — Christopher L Templeton
(74) *Attorney, Agent, or Firm* — Armstrong Teasdale LLP

(57) ABSTRACT

One exemplary device includes a tubular structure having proximal and distal ends and at least one layer of braided material configured to facilitate thrombosis. The tubular structure includes an end section at the proximal or distal end having a cross-sectional dimension that is larger than that of an opening of the target site. The device also includes a stiffener wire coupled to the tubular structure, and the wire is configured to extend at least partially through the opening and facilitate securing the end section over the opening. The tubular structure and stiffener wire include respective preset, expanded configurations and are configured to be constrained to respective reduced configurations for delivery to the target site and to at least partially return to their respective preset, expanded configurations at the target site when unconstrained.

48 Claims, 5 Drawing Sheets

(52) U.S. Cl.
CPC .............. *A61B 2017/00623* (2013.01); *A61B 2017/00867* (2013.01); *A61M 25/00* (2013.01)

(56) References Cited

U.S. PATENT DOCUMENTS

| | | | |
|---|---|---|---|
| 5,846,261 A * | 12/1998 | Kotula | A61B 17/0057 606/213 |
| 5,861,003 A | 1/1999 | Latson et al. | |
| 5,944,738 A | 8/1999 | Amplatz et al. | |
| 5,976,174 A | 11/1999 | Ruiz | |
| 6,056,769 A * | 5/2000 | Epstein et al. | 606/213 |
| 6,056,770 A * | 5/2000 | Epstein et al. | 606/213 |
| 6,059,812 A | 5/2000 | Clerc et al. | |
| 6,254,592 B1 * | 7/2001 | Samson et al. | 606/1 |
| 6,267,775 B1 | 7/2001 | Clerc et al. | |
| 6,346,117 B1 | 2/2002 | Greenhalgh | |
| 6,350,270 B1 * | 2/2002 | Roue | 606/151 |
| 6,368,338 B1 | 4/2002 | Konya et al. | |
| 6,368,339 B1 * | 4/2002 | Amplatz | 606/200 |
| 6,375,668 B1 * | 4/2002 | Gifford et al. | 606/200 |
| 6,464,712 B1 * | 10/2002 | Epstein et al. | 606/213 |
| 6,656,207 B2 * | 12/2003 | Epstein et al. | 606/213 |
| 6,932,830 B2 * | 8/2005 | Ungs | 606/200 |
| 7,153,323 B1 * | 12/2006 | Teoh et al. | 623/1.23 |
| 7,678,135 B2 * | 3/2010 | Maahs | A61B 17/0401 606/198 |
| 7,695,488 B2 * | 4/2010 | Berenstein et al. | 606/194 |
| 2002/0165572 A1 * | 11/2002 | Saadat | 606/194 |
| 2004/0133222 A1 * | 7/2004 | Tran | A61B 17/12022 606/157 |
| 2005/0043759 A1 * | 2/2005 | Chanduszko | 606/213 |
| 2005/0121043 A1 * | 6/2005 | Abrams | 128/887 |
| 2005/0251154 A1 | 11/2005 | Chanduszko et al. | |
| 2005/0267525 A1 | 12/2005 | Chanduszko | |
| 2005/0273119 A1 | 12/2005 | Widomski et al. | |
| 2006/0155303 A1 | 7/2006 | Konya et al. | |
| 2006/0241690 A1 * | 10/2006 | Amplatz et al. | 606/213 |
| 2007/0250081 A1 | 10/2007 | Cahill et al. | |
| 2007/0265656 A1 * | 11/2007 | Amplatz et al. | 606/200 |
| 2007/0270891 A1 * | 11/2007 | McGuckin, Jr. | 606/157 |
| 2008/0200945 A1 * | 8/2008 | Amplatz et al. | 606/195 |
| 2008/0262518 A1 | 10/2008 | Freudenthal | |

* cited by examiner

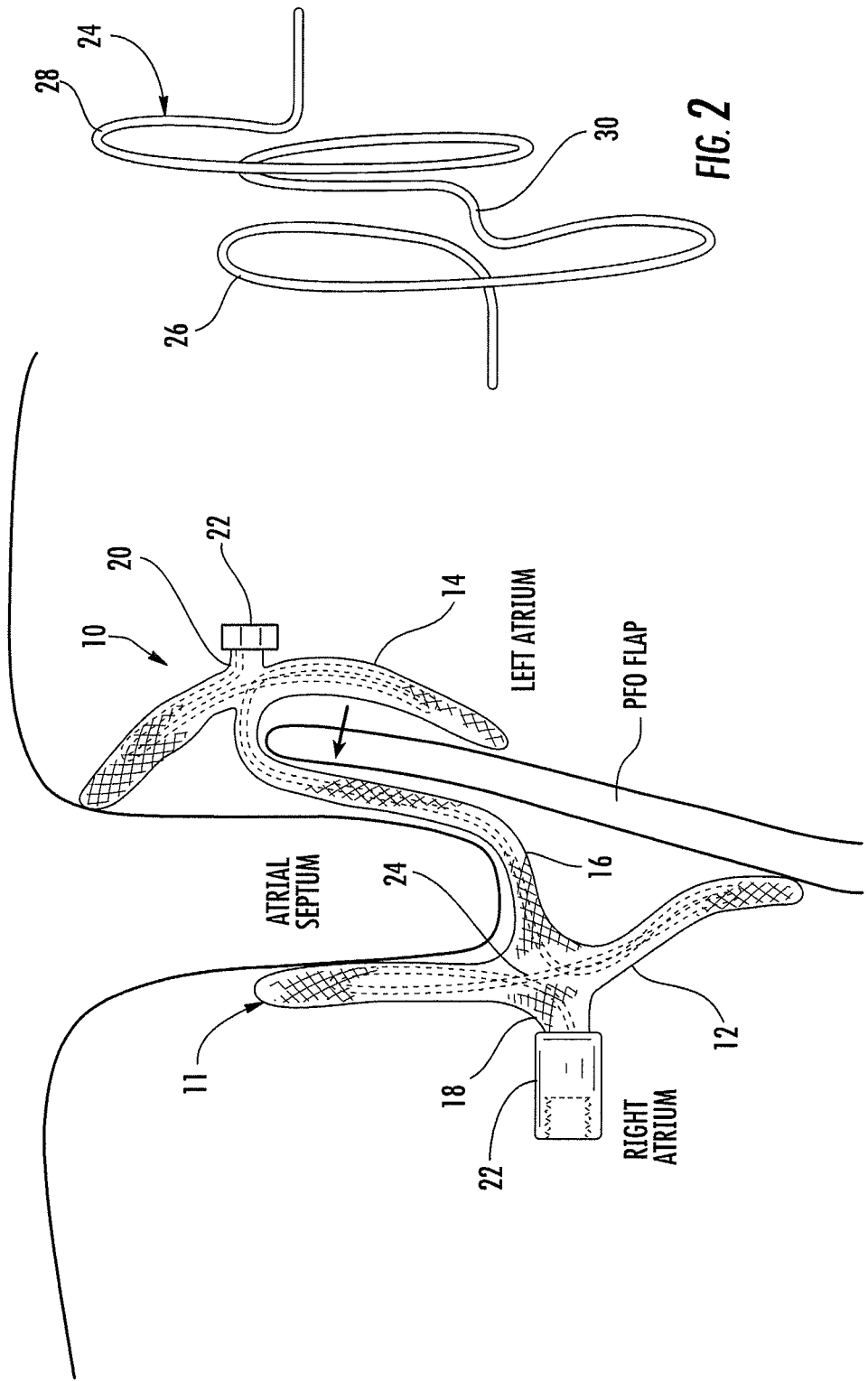

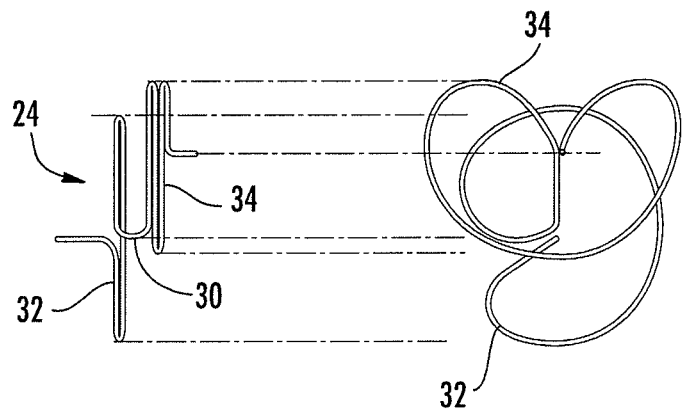
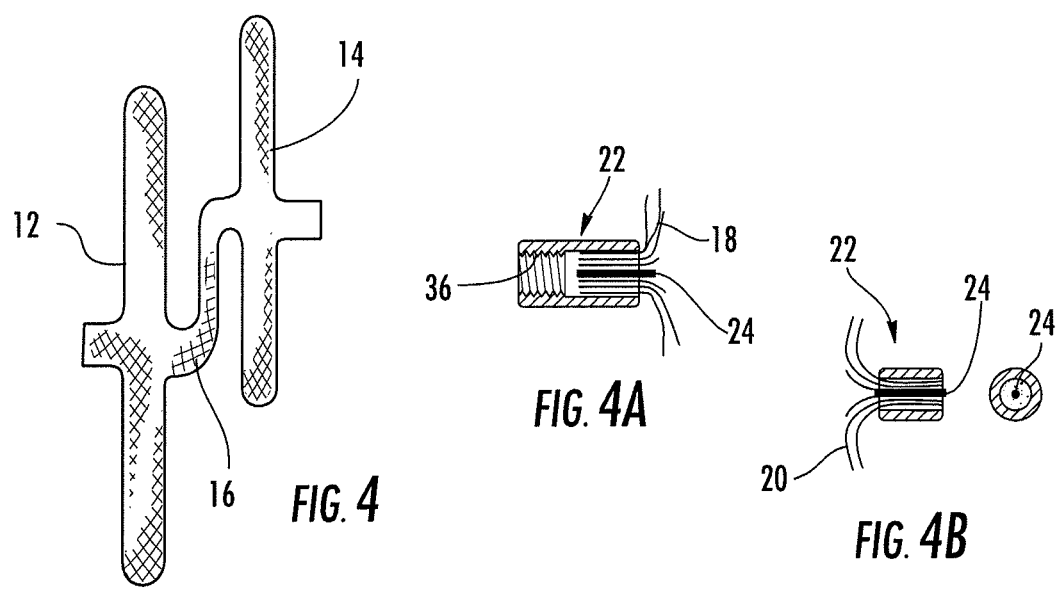
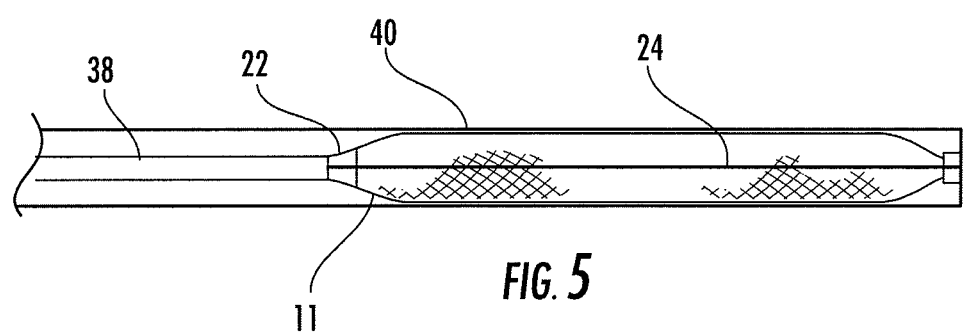

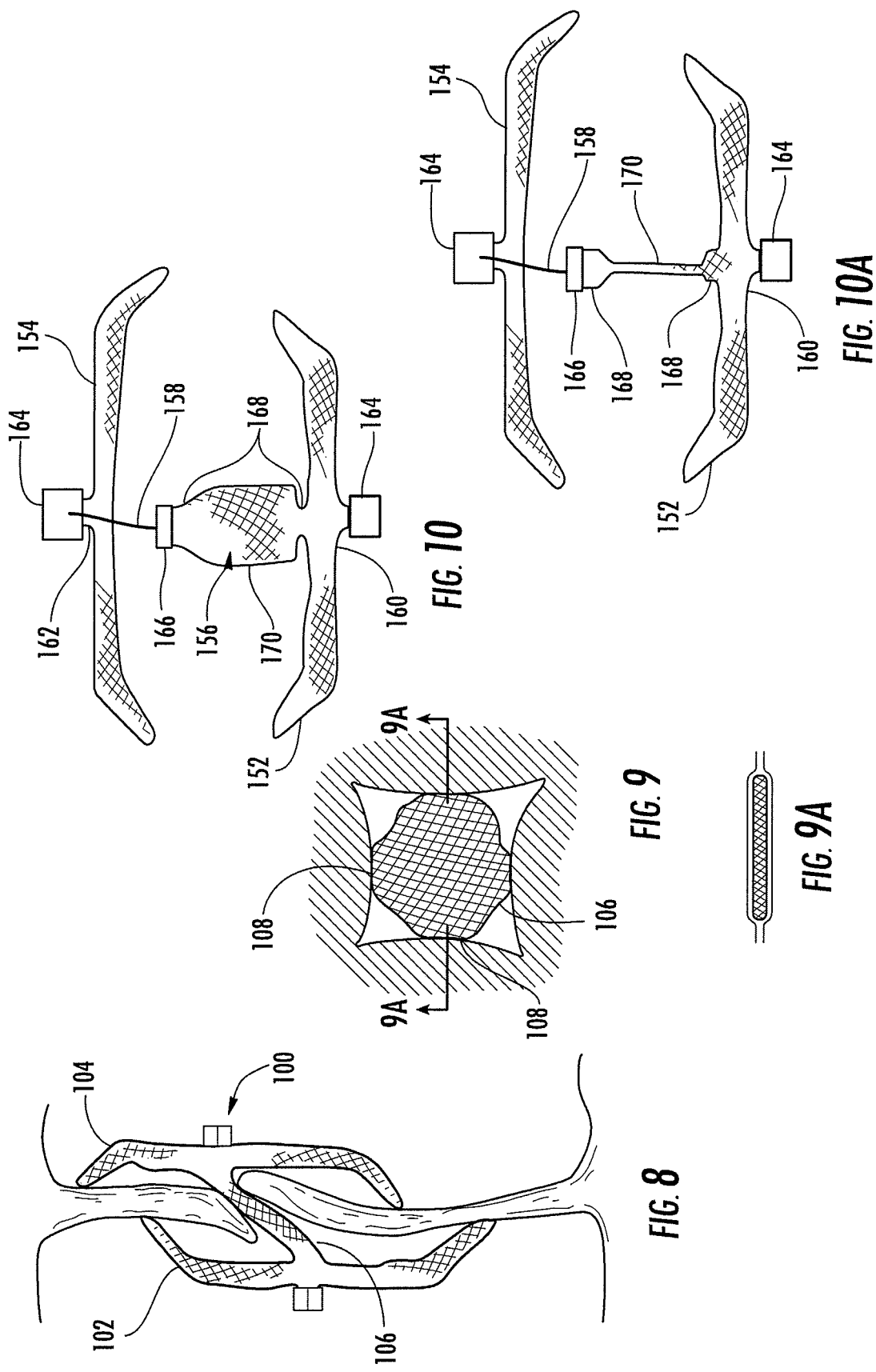

MEDICAL DEVICE WITH STIFFENER WIRE FOR OCCLUDING VASCULAR DEFECTS

BACKGROUND OF THE INVENTION

I. Field of the Invention

The present invention generally relates to devices for treating various medical conditions and, more particularly, relates to occlusion devices for treating various target sites within a patient's body.

II. Description of the Related Art:

A wide variety of intracardiac prosthetic devices are used in various medical procedures. For example, certain intravascular devices, such as catheters and guide wires, are generally used to deliver fluids or other medical devices to specific locations within the vascular system of a patient, such as a selective coronary artery. Other devices are used in treating specific conditions, such as devices used in removing vascular occlusions or for treating septal defects and the like. For example, devices have been developed for treating abnormalities, such as an Atrial Septal Defect (ASD), a Ventricular Septal Defect (VSD), a Patent Ductus Arteriosus (PDA), a Patent Foramen Ovale (PFO), a Left Atrial Appendage (LAA), an Arterial Venous Malformation (AVM), as well as conditions that result from previous medical procedures such as Para-Valvular Leaks (PVL) following surgical valve repair or replacement.

Generally, a PFO is a condition where an abnormal opening is present in the septal wall between the left and right atria. In particular, the PFO typically has a tunnel passageway extending between the right and left atria that is defined between the atrial septum and the PFO flap. Under certain conditions, such as when a person coughs, the pressure in the right atrium can rise above the pressure in the left atrium causing blood to momentarily flow from the right atria to the left atria. In some patients, blood clots may collect in the PFO or near the right atrial PFO opening. Blood flowing from the right to the left atria through the tunnel opening may carry a blood clot into the left atrium. If such a clot were to flow to an artery in the head, a stroke may occur when the blood clot obstructs blood flow to the brain. It is also suggested that migraine headaches may be related to the existence of a PFO. Closing a PFO may prevent or reduce the risk of a stroke and may reduce the frequency or intensity of migraine headaches. The PFO abnormally tunnel shaped opening normally does not extend perpendicularly through the septal wall, but is oriented obliquely to substantially parallel to the atrial septum. Devices have been developed to occlude the tunnel by employing a pair of closely spaced interconnected disks that are configured to be disposed within the left and right atria on either side of the tunnel. However, because the PFO tunnel lies in an oblique plane with respect to the openings of the tunnel, the disks may be urged into coaxial alignment with one another, which may distort the PFO tunnel walls causing the PFO flap to lie in other than a flat plane. This distortion of the PFO flap makes for a more challenging opening to seal. Various designs have been proposed to account for closing a PFO tunnel and PFO distortion. One such design is one having an elastic elongated central member that extends through the PFO tunnel length, connecting and urging the disk members on either side of the atrial septum toward each other to occlude the PFO. Although this design allows for the variation in tunnel length and eccentricity of the openings, the clamping force is applied in line with the tunnel as opposed to direct clamping more perpendicular to the disks. As a result, some distortion of the PFO flap may occur. In such a design, the clamping force is determined by the configuration of the elastic central member, the wire diameter, and number of wires.

Accordingly, it would be advantageous to provide a medical device that is both easy to deploy through a lower profile catheter and that can be accurately placed in a target site, such as a PFO with minimal distortion of the PFO flap or tunnel, while providing improved clamping force for a more effective seal and fixation. It would also be desirable to have a medical device having a softer sealing surface to minimize atrial/septum tissue abrasion while still providing adequate clamping forces. It would also be advantageous to have a medical device design that allows for selective clamping force at selective locations about a target site, such as the PFO. In addition, there exists a need for a medical device for occluding a target site that provides rapid occlusion following delivery and placement thereof.

SUMMARY OF THE INVENTION

Embodiments of the present invention may provide improvements over the prior art by, among other things, providing devices and methods for treating various target sites, such as vascular abnormalities. For example, a device according to one embodiment includes a tubular structure having proximal and distal ends and at least one layer of braided material configured to facilitate thrombosis. The tubular structure includes an end section at the proximal or distal end having a cross-sectional dimension that is larger than that of an opening of the target site. The device also includes a stiffener wire coupled to the tubular structure, wherein the wire is configured to extend at least partially through the opening and facilitate securing the end section over the opening. The tubular structure and stiffener wire include respective preset, expanded configurations and are configured to be constrained to respective reduced configurations for delivery to the target site and to at least partially return to their respective preset, expanded configurations at the target site when unconstrained.

According to various aspects, the end section is disk shaped and/or the tubular structure may have an end section at each of the proximal and distal ends. The end sections may be disposed non-coaxially with respect to one another in the preset, expanded configuration. The tubular structure may include a central portion extending between the end sections and that is configured to extend through a tunnel of a patent foramen ovale, wherein the central portion has a cross-sectional dimension that may be at least as large as that of the tunnel. Each of the end sections may have a cross-sectional dimension that is larger than a cross-sectional dimension of the central portion, wherein each end section is configured to cover a respective opening of the tunnel. In addition, the stiffener wire may be flexible and couple one of the end sections to the central portion such that the coupled end section is configured to articulate about the stiffener wire. The stiffener wire may be disposed within and between the end sections. One of the end sections may be configured to cover an opening of a tunnel of a patent foramen ovale in the right atrium, and the other end section may be configured to cover an opening of the tunnel in the left atrium.

According to further aspects, the at least one layer of fabric includes a plurality of braided strands. The tubular structure and stiffener wire may include a shape memory material. Furthermore, the medical device may include a pair of end clamps for securing each of the proximal and distal ends of the tubular structure. The proximal and/or distal end of the stiffener wire may also be secured with one or both of the end clamps.

Additional aspects include a medical device having a stiffener wire that is configured to apply a clamping force to the end section made from a stiffer material than the tubular structure. The stiffener wire may be at least partially disposed within the tubular structure. Moreover, the stiffener wire may include one or more loops within the tubular structure in the preset, expanded configuration, such as within the end section, and be configured to extend over the opening in the preset, expanded configuration. The stiffener wire may extend distally of the distal end of the tubular structure in the preset, expanded configuration. In addition, the tubular structure and stiffener wire may be configured to be elongated to approximately the same length in the reduced configuration. The stiffener wire may be configured to extend through a tunnel of a patent foramen ovale, wherein the end section is configured to at least partially radially surround an opening of the tunnel in the right atrium. The stiffener wire may further be configured to extend through the tunnel of a patent foramen ovale and extend over an opening of the tunnel in the left atrium. The stiffener wire may have a diameter that varies along the length of the wire. Moreover, the tubular structure may include a central portion extending between the end sections, wherein the stiffener wire extends both inside and outside of the central portion and extends radially outwardly therefrom for facilitating engagement with the target site. The medical device may include a plurality of stiffener wires spaced circumferentially about the central portion and extending radially outwardly therefrom, wherein each stiffener wire is configured to engage the target site.

An additional embodiment of the present invention is directed to a method for delivering a medical device to a target site. The method includes providing a medical device as described above. In addition, the method includes constraining the medical device from an initial, expanded configuration to a reduced configuration and positioning the constrained medical device in a catheter. The method further includes delivering the constrained medical device to the target site and deploying the constrained medical device from the catheter such that the medical device at least partially returns to the initial, expanded configuration at the target site and the end section covers the opening of the target site.

According to aspects of the method, the providing step includes providing a tubular structure having an end section at each of the proximal and distal ends. The deploying step may include deploying the medical device such that the end sections are disposed non-coaxially with respect to one another. The deploying step may also include deploying the medical device such that one of the end sections is configured to cover an opening of a tunnel of a patent foramen ovale in the right atrium, and the other end section is configured to cover an opening of the tunnel in the left atrium. The deploying step may also include controlling and positioning the angular orientation of the device relative to the PFO tunnel. The providing step may include providing a tubular structure comprising a central portion extending between the end sections and that is configured to extend through a tunnel of a patent foramen ovale, wherein the central portion has a cross-sectional dimension at least as large as that of the tunnel. Furthermore, the deploying step may include deploying the medical device such that the central portion extends through and engages a tunnel of a patent foramen ovale.

Additional aspects of the method include providing a stiffener wire disposed within the end section, wherein the deploying step includes deploying the medical device such that the stiffener wire extends over the opening in the initial, expanded configuration. The deploying step may alternatively include deploying the medical device such that the stiffener wire extends through a tunnel of a patent foramen ovale and the end section covers an opening of the tunnel in the right atrium. Furthermore, deploying may include deploying the medical device such that the stiffener wire extends through the tunnel of the patent foramen ovale and over an opening of the tunnel in the left atrium. The constraining step may include elongating the tubular structure and stiffener wire to approximately the same length in the reduced configuration. The deploying step may include deploying the medical device such that the stiffener wire applies a clamping force to the end section.

One embodiment of the present invention is directed to a medical device for treating a target site that includes a tubular structure comprising proximal and distal ends and at least one layer of braided material configured to facilitate thrombosis. The tubular structure includes an end section at each of the proximal and distal ends having a cross-sectional dimension larger than that of an opening of the target site, and the tubular structure further includes a central portion extending between the end sections. The medical device also includes a stiffener wire having proximal and distal ends and positioned within each of the end sections and the central portion. The tubular structure and stiffener wire have an initial, expanded configuration, wherein the tubular structure and stiffener wire are configured to be constrained from the initial, expanded configuration to a reduced configuration for delivery to the target site and to at least partially return to the initial, expanded configuration at the target site when unconstrained, and wherein the stiffener wire is configured to ensure that the end sections are axially offset from one another in the initial, expanded configuration.

According to various aspects of the medical device, the central portion may have a cross-sectional dimension at least as large as that of the tunnel. The medical device may further include a pair of end clamps, wherein each of the proximal and distal ends of the at least one tubular structure is secured with a respective end clamp. The proximal and distal ends of the stiffener wire may be secured with respective end clamps. Moreover, the stiffener wire may include one or more loops within the tubular structure in the initial, expanded configuration, and the one or more loops may be disposed within each end section and have a cross-sectional dimension larger than that of an opening of the target site. The stiffener wire may include a stiffer material than the tubular structure and be configured to apply a clamping force between the end sections. The tubular structure and stiffener wire may each include a shape memory material having an initial, expanded configuration corresponding to a preset, expanded configuration, wherein the tubular structure and stiffener wire are configured to be constrained from their preset, expanded configurations to respective reduced configurations for delivery to the target site and to self-expand and at least partially return to their respective preset, expanded configurations at the target site when unconstrained.

An additional embodiment of the present invention is also directed to a medical device for treating a target site. The medical device includes a tubular structure having proximal and distal ends and at least one layer of braided material configured to facilitate thrombosis. The tubular structure includes an end section at the proximal or distal end having a cross-sectional dimension larger than that of an opening of the target site. In addition, the medical device includes a stiffener wire coupled to an opposite end of the tubular structure from that of the end section and including one or more loops, wherein the one or more loops have a cross-sectional dimension larger than that of an opening of the target site. The tubular structure and stiffener wire have an initial, expanded configuration, wherein the tubular structure and stiffener wire are configured to be constrained from the initial, expanded configuration to a reduced configuration for delivery to the target site and to at least partially return to the initial, expanded configuration at the target site when unconstrained.

Aspects of the medical device include a tubular structure having an end section that is configured to cover an opening of a tunnel of a patent foramen ovale in the right atrium, wherein the one or more loops of the stiffener wire are configured to at least partially surround an opening of the tunnel in the left atrium. The stiffener wire may be at least partially disposed within the tubular structure and/or the stiffener wire may include a plurality of loops. The end section and the one or more loops of the stiffener wire may be disposed non-coaxially with respect to one another in the initial, expanded configuration. As before, the tubular structure and stiffener wire may each include a shape memory material having an initial, expanded configuration corresponding to a preset, expanded configuration, wherein the tubular structure and stiffener wire are configured to be constrained from their preset, expanded configurations to respective reduced configurations for delivery to the target site and to self-expand and at least partially return to their respective preset, expanded configurations at the target site when unconstrained.

BRIEF DESCRIPTION OF THE DRAWINGS

The foregoing features and advantages of the invention will become apparent to those skilled in the art from the following detailed description of a preferred embodiment, especially when considered in conjunction with the accompanying drawings in which like numerals in the several views refer to corresponding parts.

FIG. 1 is a side elevation view of an occluder device positioned within a PFO according to one embodiment of the present invention;

FIG. 2 is a side elevation view of a stiffener wire according to an embodiment of the present invention;

FIG. 3A is a side elevation view of a stiffener wire according to another embodiment of the present invention FIG. 3B is an end view of the stiffener wire shown in FIG. 3A;

FIG. 4 is a side elevation view of a tubular member according to one embodiment of the present invention;

FIG. 4A is a cross-sectional view of an end clamp according to one embodiment of the present invention;

FIG. 4B is a cross-sectional view of an end clamp according to another embodiment of the present invention;

FIG. 5 is a side elevation view of a medical device positioned within a delivery catheter according to one embodiment of the present invention;

FIG. 8 is a side elevation view of an occluder device positioned within a PFO according to an additional embodiment of the present invention;

FIG. 9 is a cross-sectional view of a central portion positioned within a PFO tunnel according to one embodiment of the present invention;

FIG. 9A is cross-sectional view of the central portion show in FIG. 9;

FIG. 10 is a side elevation view of an occluder device according to one embodiment of the present invention;

FIG. 10A is another side elevation view of the occluder device shown in FIG. 10.

DETAILED DESCRIPTION OF THE PREFERRED EMBODIMENTS

Figure 6:
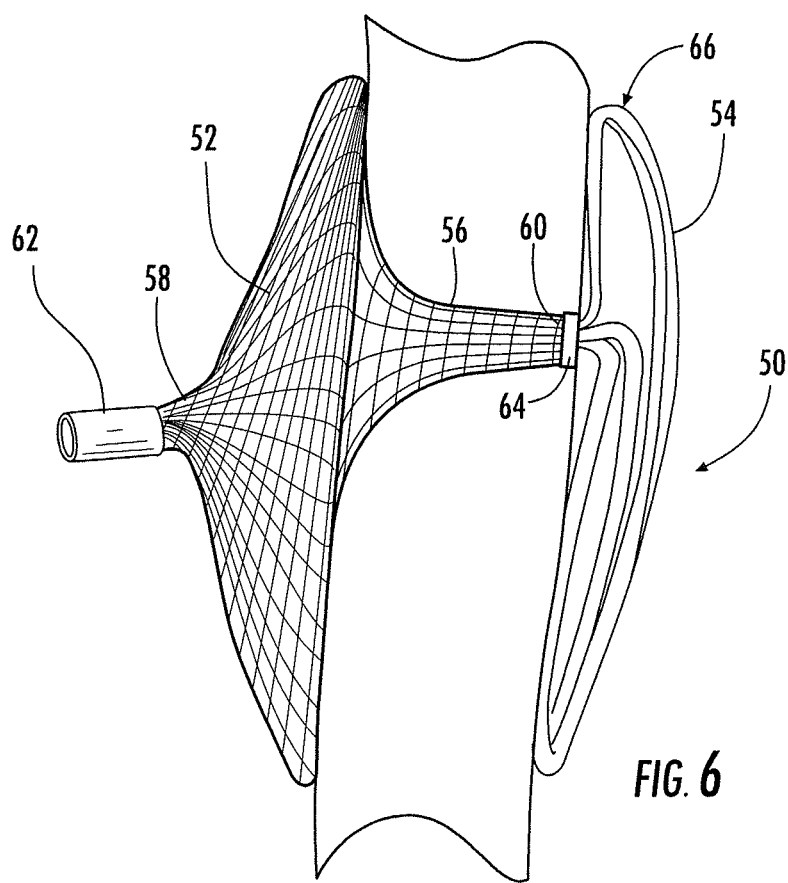
FIG. 6 is a side elevation view of an occluder device positioned within a target site according to another embodiment of the present invention.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a medical device for use in treating a target site within the body, such as occluding various vascular abnormalities, which may include, for example, occluding an Arterial Venous Malformation (AVM), an Atrial Septal Defect (ASD), a Ventricular Septal Defect (VSD), a Patent Ductus Arteriosus (PDA), a Patent Foramen Ovale (PFO), a Left Atrial Appendage (LAA), an Arterial Venous Malformation (AVM), as well as conditions that result from previous medical procedures such as Para-Valvular Leaks (PVL) following surgical valve repair or replacement, and the like. It is understood that the use of the term "target site" is not meant to be limiting, as the device may be sized and configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a congenital defect, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, a septum, or the like.

According to one embodiment and described in greater detail below, a medical device for treating a target site is provided, wherein at least a portion of the medical device includes a tubular structure of a braided material and a stiffener wire sized and configured to facilitate securing the medical device at the target site. For example, the medical device may include a disk-shaped end section that is sized and configured to overlie an opening of the target site (e.g., an opening of a PFO, ASD or VSD), and the stiffener wire may be sized and configured to secure the end section over the opening. Both the tubular structure and stiffener wire may include a preset, expanded configuration and may be sized and configured to be constrained to a reduced configuration for delivery to the target site and at least partially return to their preset, expanded configuration when unconstrained. In one embodiment, the medical device includes a pair of end sections that are not coaxially aligned with one another, thereby facilitating fixation within a target site such as the PFO without distorting the PFO flap.

As used herein, the term "disk" is not meant to be limiting and may be a member having a circular, an oval, a discoid, or other shape having a cross sectional dimension configured to overlie an opening for substantially precluding or impeding flow through the opening.

According to one embodiment of the present invention for forming a medical device of the invention, the device includes a braided fabric formed of a plurality of wire strands having a predetermined relative orientation with respect to one another. However, it is understood that according to additional embodiments of the present invention, the device may be formed using various techniques. For example, the device could be etched or laser cut from a tube such as to form an interstice geometry, or the device could comprise an occlusion material coupled to a scaffolding structure or a plurality of slices of a tubular member coupled together, such as via gluing. Moreover, it is understood that the device may comprise one or more layers of occluding material such that the device may be a variety of occluding materials capable of at least partially inhibiting blood flow therethrough in order to facilitate the formation of thrombus and epitheliazation around the device.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

As used herein, "substantially preclude or impede flow" shall mean, functionally, that blood flow may occur for a short time, e.g., about 3-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the device and if no contrast media flows through the wall of the device after a predetermined period of time as viewed by fluoroscopy, then the position and occlusion of the device is adequate. Moreover, occlusion of the vascular abnormality could be assessed using various echo modalities.

As used herein the term "proximal" shall mean closest to the operator (less into the body) and "distal" shall mean furthest from the operator (further into the body). In positioning of the medical device from a downstream access point, distal is more upstream and proximal is more downstream.

According to one embodiment, the occlusive material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. It is also understood that the device may comprise various materials other than Nitinol that have elastic properties, such as spring stainless steel, trade named alloys such as Elgiloy®, Hastelloy®, CoCrNi alloys (e.g., trade name Phynox), MP35N®, CoCrMo alloys, or a mixture of metal and polymer fibers. Polymer fibers may include monofilaments or multifilament yarns ranging from about 10-400 denier. Individual filaments may range from about 0.25 to 10 denier. Polymers may be composed of PET (Dacron), polyester, polypropylene, polyethylene, HDPE, polyurethane, silicone, PTFE, polyolefins and ePTFE. The metal and plastic fibers may be combined in the same layer, or the tubular layers may be constructed in such a manner that each layer is made from a different material. The polymer layer may be a multifilament braided layer or may be composed of at least one filament or yarn wound about a mandrel with a pitch and diameter similar to other adjacent layers and may be positioned about or inside another adjacent layer or between adjacent layers. Depending on the individual material selected, the wire strand diameter, number of wire strands and pitch may be altered to achieve the desired properties of the device. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One can solder, braze, weld, coat, glue, clamp, tie or otherwise affix the ends of the desired length together (e.g., with a biocompatible cementitious organic material).

In addition, a plurality of layers of occlusive material could be separately woven into tubular members, with each tubular member coaxially disposed within another tubular member. For further discussion regarding an exemplary multi-layer device and techniques for fabricating such a device, see U.S. Patent Appl. Publ. No. 2007/0265656 to Amplatz et al., which is hereby incorporated in its entirety by reference.

According to one embodiment, each layer of the device may comprise 36-144 wire strands ranging in diameter from about 0.001 to 0.012 in. formed of a shape memory alloy, such as Nitinol, that are braided so as to define fenestrations with an area of about 0.00015 to 0.01 sq. in., which are sufficiently small so as to slow the blood flow through the wall of the device and to facilitate thrombus formation thereon. Inner and outer braided layers may have pitch angles that are about equal to obtain desirable collapse and expansion characteristics, such as maintaining a uniform overall length.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element should be selected to deform the fabric into substantially the shape of the desired medical device when unconstrained. Once the molding element is assembled with the metal fabric generally conforming to a molding surface of that element, the fabric can be subjected to a heat treatment while it remains in contact with that molding surface. After the heat treatment, the fabric is removed from contact with the molding element and will substantially retain its heat set shape in a deformed state.

Those skilled in the art will appreciate that in order to speed up the occlusion of the vessel device, the device may be coated with a suitable thrombogenic agent, filled with a polyester fiber, braided with an increased number of wire strands, or include multiple layers of fabric. The interwoven fiber may attach to a clot to retain the clot firmly within the device as it forms the occlusion.

The device may include a plurality of planes of occlusion. A plane of occlusion may be any surface, whether flat or irregular in shape, that may be oriented generally transverse to the flow of blood so as to facilitate the formation of thrombus. For example, an umbrella shaped plane, even with two layers adhered together on the front and back of a skeleton frame, would be projected as one plane of occlusion. Whereas a device with two umbrella structures, each with their own occlusive material adhered thereto, would project into two planes of occlusion. At least one plane of occlusion may include one or more layers of occlusive material, such as a layer of fabric and/or a layer of polyester fiber, two layers of metal, or two layers of polyester. Thus, by modifying the configuration of the device, the number of planes of occlusion may be modified, and by changing the number of layers of occlusive material, the rate at which the device occludes the vascular abnormality may also be modified.

Referring now to the drawings, a discussion of the embodiments of the medical device of the present invention will next be presented. FIG. 1 illustrates a first embodiment of a medical device 10 for treating a target site, such as a PFO. In particular, the medical device 10 includes a tubular member 11 having a pair of end sections 12, 14 and a central portion 16 extending therebetween. The end sections 12, 14 typically have a larger cross-sectional dimension than that of the central portion 16. The end sections 12, 14 may be disk shaped or other shape sized and configured to overlie an opening of a target site. For example, FIG. 1 shows that one or both of the end sections 12, 14 may be disk shaped and may also have a concave surface facing the septum.

The end sections 12, 14 and central portion 16 may be formed from a single tubular member 11. As described above, the tubular member 11 may be formed from one or more layers of braided fabric with each layer including a plurality of strands. The proximal 18 and distal 20 ends of the medical device 10 may be secured with respective end clamps 22. For instance, FIGS. 4A and 5 illustrate that an end clamp 22 having threads 36 for engagement with a delivery device 38 may be used to secure the terminating ends of the braided strands at the proximal end 18 of the medical device 10. In addition, FIG. 4B depicts an end clamp 22 that may be employed to secure the terminating ends of the braided strands at the distal end 20 of the medical device 10. It is understood that either of the clamps 22 shown in FIGS. 4A and 4B could be used at one or both ends of the medical device 10.

FIG. 1 also illustrates that the medical device 10 includes a stiffener wire 24 extending within and between the proximal 18 and distal 20 ends. The stiffener wire 24 may also be coupled at its free ends by respective end clamps 22, as shown in FIGS. 4A and 4B. Thus, the clamps 22 may secure both the proximal 18 and distal 20 ends of the medical device 10, as well as the proximal and distal ends of the stiffener wire 24. The stiffener wire 24 may have a variety of configurations and as shown in FIGS. 2 and 3, may have a predetermined configuration for facilitating fixation of the medical device at the target site. For example, the stiffener wire 24 may have a pair of looped, coiled, spiral, or irregular portions 26, 28 sized and configured to extend through each of the end sections 12, 14, and a central portion 30 extending between the looped portions 26, 28. Thus, the tubular member 11 and stiffener wire 24 may have similar configurations in a preset, expanded configuration. Similar to the end sections 12, 14, the looped portion 26, 28 may have a larger cross-sectional dimension at its ends than that of the central portion 16 and at least partially radially surround a target site (e.g., the looped portions 26, 28 may be circular, partially circular, or any other shape configured to do so). In addition, the stiffener wire 24 may be formed of a stiffer material than that of the tubular member 11 in order to provide a clamping force between the end sections. For instance, the stiffener wire 24 may be formed of a Nitinol material and have a larger diameter than that of the individual wires of the tubular member 11.

The end sections 12, 14 and central portion 16 may be formed from a single tubular member 11 and heat set in a preset, expanded configuration as described above. For example, FIG. 4 shows the tubular member 11 in a preset, expanded configuration, wherein the end sections 12, 14 are offset and not coaxially aligned with one another, and the central portion 16 is substantially parallel to the end sections. Similarly, the stiffener wire 24 may also be heat set in a preset, expanded configuration such as that shown in FIGS. 2, 3A, and 3B. Namely, FIG. 3A shows that the stiffener wire 24 may include a first loop 32 and a second loop 34 each having a plurality of bends, wherein the loops are axially offset from one another by a central portion 30 (note that the bends of each loop 32 and 34 would be in the same plane extending out of the page in FIG. 3A). FIG. 3B demonstrates that each loop 32, 34 may have a "kidney bean" or other shape that at least partially conforms to each end section 12, 14. According to one embodiment, the tubular member 11 may be heat set such that the end sections 12, 14 are coaxially aligned. In this particular embodiment, the end sections 12, 14 may be resilient in order to conform to the configuration of the stiffener wire 24 (e.g., FIG. 2 or 3A). As such, when in a relaxed configuration, the end sections 12, 14 are capable of being disposed non-coaxially with respect to one another. Alternatively, the tubular member 11 may be formed from a resilient material (e.g., a material not having shape memory properties) that is configured to conform to an initial, expanded shape of the stiffener wire 24. For example, the tubular member 11 may be configured to conform to a preset, expanded configuration of that of the stiffener wire 24.

The tubular member 11 and stiffener wire 24 may be formed from a resilient and shape memory material such that the medical device 10 may be constrained from a preset, expanded configuration to a reduced configuration for delivery within a catheter 40 to the target site, as shown in FIG. 5 and explained in further detail below. For instance, the medical device 10 may be elongated by pulling on the proximal 18 and distal 20 ends of the device such that the tubular member 11 is constrained to a reduced diameter and the stiffener wire 24 is substantially straightened. In order to adequately reduce the profile of the tubular member 11 and stiffener wire 24, the tubular member and stiffener wire may be configured to be elongated to approximately the same length. Upon release from the catheter 40, the medical device 10 is configured to return to its preset, expanded configuration, and the delivery device 38 may be unscrewed from the threaded clamp 22 such that the device may be fully deployed. Moreover, the stiffener wire 24 is capable of applying a clamping force between the end sections 12, 14 to secure the medical device 10 at the target site.

According to one embodiment, the medical device 10 is capable of being used to occlude a PFO as shown in FIG. 1. In particular, one end section 12 is sized and configured to overlie the opening of the PFO tunnel in the right atrium, while the second end section 14 is sized and configured to overlie the opening of the PFO tunnel in the left atrium. The central portion 16 is sized and configured to extend through the PFO tunnel. The stiffener wire 24 is similarly positioned within the PFO and is configured by its preset shape to provide a clamping force such that the end portions 12, 14 are drawn toward each other and are secured over the tunnel openings. The medical device 10 is sized and configured to occlude the PFO without distorting the PFO flap since the end sections 12, 14 may be disposed non-coaxially with respect to one another and because the tubular member 11 may be formed from smaller wire diameters and hence softer material since the stiffener wire 24 provides adequate clamping force. As one example, the tubular braided fabric may be fabricated from about 72 to 144 Nitinol wires each having a diameter from about 0.001 to 0.0035 inch, and the stiffener wire may be fabricated from Nitinol wire having a diameter of about 0.005 to 0.015 inch. The specific construction of the medical device 10 may be determined by the specific body location, size of defect to be occluded, shape of the anatomy and compliance of surrounding tissue as well as other factors. As such, the softer tubular member 11 may function to occlude rather than provide primary clamping force and better conform to the target site and be less abrasive to tissue. The softer tubular member made from smaller diameter filaments may allow for lower profile and less drag through the delivery catheter enabling delivery through smaller diameter catheters, which in turn may lead to easier device placement through smaller diameter vessels or vessels having a more tortuous path not previously accessible.

It is understood that the embodiment of the medical device 10 shown in FIGS. 1-4 is not meant to be limiting, as the medical device may be various sizes and configurations according to additional aspects of the present invention. For instance, although the stiffener wire 24 is shown as being clamped at the proximal 18 and distal 20 ends of the device 10, the stiffener wire may be adjustable in length. Thus, the stiffener wire 24 may be clamped by only one clamp 22, or the stiffener wire may be configured for extension, such as with a telescoping adjustment, wherein the stiffener wire is comprised of two wire portions and a tubular sleeve member permanently connected to one wire at a point between the device ends, and wherein the tubular sleeve member has an inner diameter sufficient to accept the second wire portion in a sliding fit manner. Alternatively, one clamp member may have a tubular sleeve member affixed to the clamp to accept one end of the stiffener wire in sliding fit manner while the other end of the stiffener wire may be clamped in the other end clamp. A small spring or elastic filament may optionally extend within the tubular sleeve member to connect the wire ends under tension or a wire end to an end clamp. Moreover, the tubular member 11 and stiffener wire 24 may be various sizes and configurations for treating different target sites. For example, the end sections 12, 14 and loops 26, 28 could be axially aligned with one another. In addition, the stiffener wire 24 may be any number of configurations in order to apply an adequate clamping force, such as one or more loops. Optionally the stiffener wire 24 may be variable in diameter along its length in order to locally tailor clamping forces as desired. For instance, the wire diameter can be altered by center-less grinding or by etching to the desired dimension. The shape of the stiffener wire may ultimately depend on the application and shape of surrounding tissue.

Figure 7:
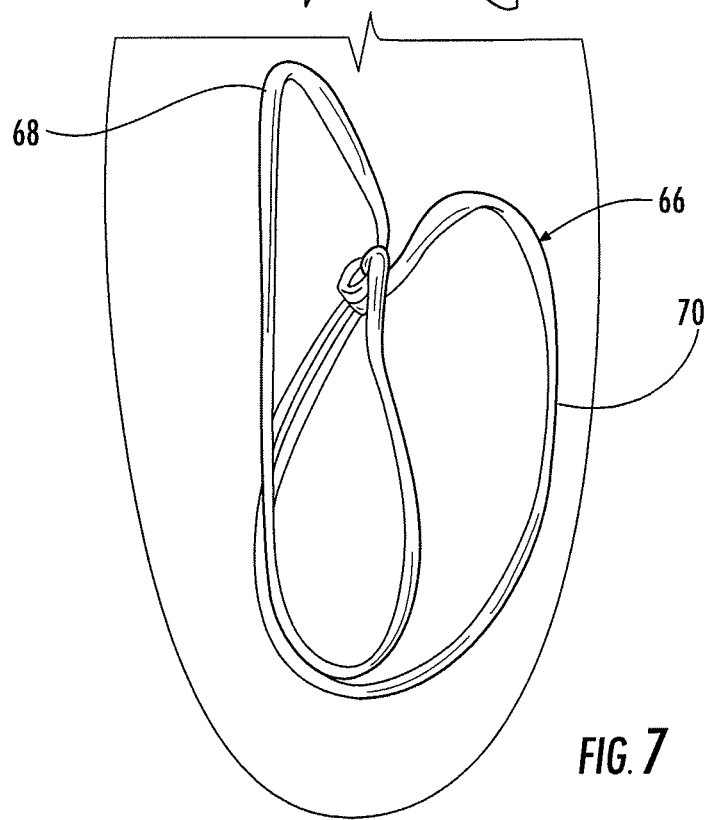
FIG. 7 is an end view of the device shown in FIG. 6.

FIGS. 6 and 7 illustrate an additional embodiment of the present invention of a medical device 50 that includes a pair of end sections 52, 54 and a central portion 56 extending therebetween. The end section 52 and central portion 56 may be formed from a single tubular member, wherein the tubular member may be formed from one or more layers of braided fabric with each layer including a plurality of strands. The end section 52 may be disk shaped or other other shape that is sized and configured to overlie an opening at the target site. Moreover, the proximal 58 end of the medical device 50 may be secured with an end clamp 62, which may be threaded for engagement with a delivery device as discussed above. The central portion 56 may also be secured with an end clamp or a marker band 64 at the distal end 60 of the central portion of the device 50.

The end section 54 may be a stiffener wire 66 configured to provide a clamping force with respect to the end section 52. The end section 54 may have a variety of configurations, such as that shown in FIGS. 6 and 7, that facilitates fixation of the medical device 50 at the target site. For example, the end section 54 may be formed by one or more loops 68, 70 of the stiffener wire 66 that is sized and configured to secure the end section at the target site. The loops 68, 70 could be a variety of shapes, such as "kidney bean", disk, oval, half-disk, or the like. One end of the stiffener wire 66 may be secured by the end clamp 62, and the opposite end of the stiffener wire may be clamped with the clamp 64. Alternatively, both ends of the stiffener wire 66 may be secured by either clamp 62 or 64. According to one embodiment, the stiffener wire 66 may be sized and configured to slide through the clamp 64.

The medical device 50 may be heat set into an expanded, preset configuration, as described above. In particular, the end section 52 and central portion 56 may be heat set to a desired configuration, while the end section 54 may be independently heat set to a desired configuration. As also discussed above, the medical device 50 may be constrained to a reduced configuration for delivery through a catheter and return to the preset, expanded configuration upon release from the catheter.

Furthermore, the medical device 50 is sized and configured to be used for treating various target sites, such as an ASD, VSD or PFO. As shown in FIGS. 6 and 7, the medical device 50 is formed with the end sections 52, 54 being near concentric. This design may be more preferred for an ASD or VSD where the opening extends substantially straight through a septum. The central portion 56 and stiffener wire 66 may be alternatively formed as in FIGS. 1 and 3A-B to pass through a PFO tunnel while applying clamping force with minimal distortion to the PFO flap and openings. As before, one end section 52 is sized and configured to overlie or otherwise surround the opening of the ASD, VSD or PFO tunnel in the right atrium or ventricle as applicable, while the other end section 54 is sized and configured to overlie and/or at least partially radially surround the opening of the PFO tunnel in the left atrium or ventricle as applicable. The central portion 56 is sized and configured to extend through the septal opening or PFO tunnel, and the stiffener wire 66 may be configured to provide a clamping force such that the end portions 52, 54 are secured over the openings.

FIG. 8 depicts another embodiment of a medical device 100. The embodiment shown in FIG. 8 is similar to that of FIG. 1 but includes an alternative configuration of the central portion 106. As before, the central portion 106 extends between a pair of end sections 102, 104, but the central portion is sized and configured to conform to the target site, such as the PFO tunnel. In particular, the central portion 106 includes a round, rectangular, oval, or flat ribbon like cross-sectional dimension in the plane of the PFO tunnel that is at least as large as the cross-sectional dimension of the tunnel or target site. Thus, the central portion 106 may be sized and configured to engage and substantially fill the tunnel or target site. For instance, FIGS. 9 and 9A show cross-sectional views of the central portion 106 positioned within a PFO tunnel, wherein the central portion substantially conforms to a generally rectangular PFO cross section. In particular, FIG. 9 shows that the central portion 106 may have relatively rounded portions 108 and flat portions 110 that engage each surface of the PFO tunnel, while FIG. 9A shows that the central portion may have a thin profile for conforming to the thin profile of the PFO tunnel. However, it is understood that the central portion 106 may be resilient to conform to a variety of target sites, which may be useful for target sites such as the PFO tunnel that has a cross section that may vary from patient to patient. Because the PFO tunnel is substantially filled, the medical device 100 may provide improved fixation and occlusion within the PFO tunnel, as well as result in less PFO distortion.

FIGS. 10 and 10A illustrate an additional embodiment where a medical device 150 includes a pair of end sections 152, 154 and a central portion 156 extending therebetween. As before, the end sections 152, 154 and central portion 156 may be formed of one or more layers of braided fabric and may be formed from the same tubular member. The proximal 160 and distal 162 ends of the device 150 may be secured with respective end clamps 164. In addition, the central portion 156 may be sized and configured to fill a target site, such as the PFO tunnel. Namely, FIGS. 10 and 10A show that the central portion 156 may have a thin or flat cross section similar to that shown in FIGS. 9 and 9A and that the central portion may have waist portions 168 that are of a reduced diameter in one view shown in FIG. 10 and of a larger rounded diameter compared to the flat portion 170 in a second view shown in FIG. 10A.

Furthermore, the end section 154 may be coupled to the central portion 156 with a tether 158. The tether 158 may a flexible wire member that allows the end section 154 to articulate thereabout. For example, the tether 158 could be formed from the same tubular member as that of the end sections 152, 154 and central portion 156. Thus, the tether 158 may comprise one or more strands of braided fabric. Alternatively, the tether 158 could be a separate wire having one end attached to the clamp 164 at the distal end 162 and an opposite end attached to the central portion 156 with a clamp 166 or to the clamp 164 at the proximal end 160. According to one embodiment, the end section 154 may be configured to articulate about the tether 158 and thereby overlie and seal the opening of the PFO tunnel. It is understood that the proximal end 160 of the device 150 could also or alternatively include a tether 158 that couples the end section 152 to the central portion 156 such that either or both end sections 152, 154 may articulate about respective tethers. The tether may be shaped to apply a clamping load between the end sections 152, 154.

Figure 11:
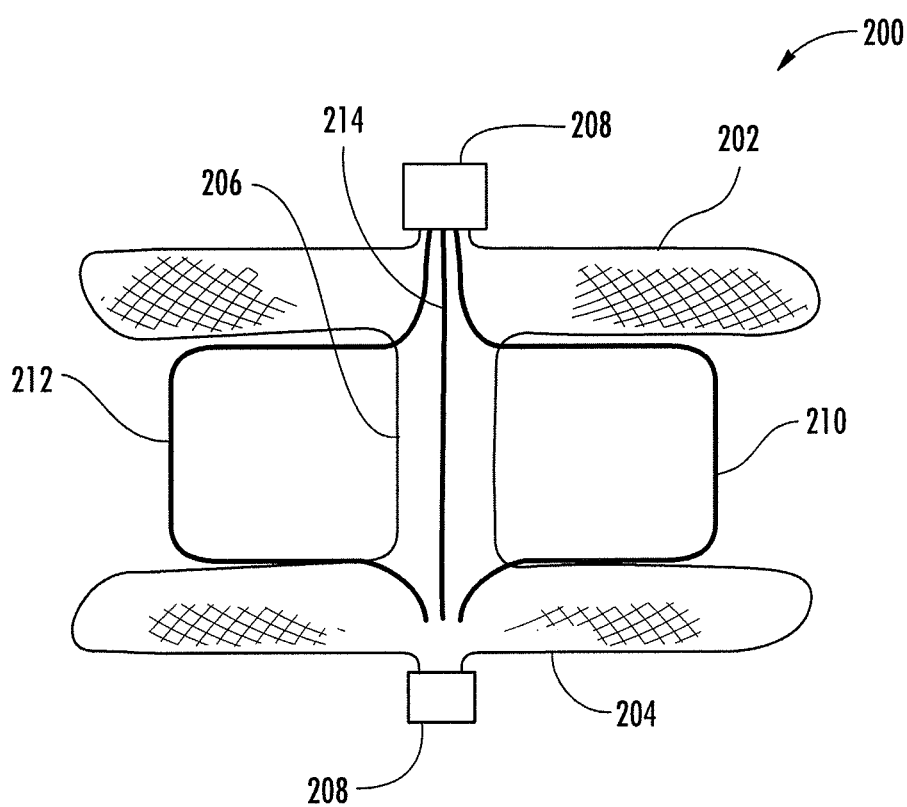
FIG. 11 is a side elevation view of an occluder device according to another embodiment of the present invention.

FIG. 11 shows a medical device 200 according to another embodiment of the present invention. The medical device 200 includes a pair of end sections 202, 204 and a central portion 206 extending therebetween. The medical device 200 may include one or more layers of braided fabric, with the ends of the braided fabric secured with respective end clamps 208. Furthermore, the medical device 200 includes at least one stiffener wire 210, 212, 214 that extends from one of the end clamps 208 and at least partially though the central portion 206. The diameter of each of the stiffener wires 210, 212, 214 is typically larger than that of the individual strands of the braided fabric. As described above, the medical device 200, including the stiffener wires 210, 212, 214, may be formed from a resilient and shape memory material such that the medical device may be constrained from a preset, expanded configuration to a reduced configuration for delivery within a catheter to the target site.

A first stiffener wire 210 extends within the end section 202, exits the braided fabric in the central portion 206, and then reenters the central portion proximate to the opposite end section 204. The medical device 200 includes a second stiffener wire 212 that is positioned opposite of the first stiffener wire. In addition, a third stiffener wire 214 extends from the end clamp 208 and axially through the central portion 206. There may be any number of stiffener wires 210, 212 spaced circumferentially about the central portion 206 and extending radially outwardly therefrom for engaging the target site. Thus, the first 210 and second 212 stiffener wires lower the number of contact points within the target site when compared to conventional medical devices having solid central portions. Minimizing the surface area of contact with the target site may be beneficial for sites that are more sensitive, such as near the HIS bundle where excessive pressure can disrupt the electrical signals to the heart. Although there is less surface area in contact with the target site, the central portion 206 has a smaller cross-sectional dimension and strand diameter for facilitating the requisite amount of flexibility and tilt for aligning the medical device 200 in the target site.

It is understood that the medical device 200 shown in FIG. 11 is not meant to be limiting, as the medical device may have various alternative aspects according to additional embodiments. Thus, the medical device 200 may include one or more stiffener wires 210, 212, 214, although three stiffener wires are illustrated. For example, the medical device 200 may include a single stiffener wire 210 that has a plurality of loops encircling the central portion 206 or is woven in and out of the central portion. In addition, even though the stiffener wires 210, 212, 214 are shown as extending partially between the proximal and distal ends of the medical device 200, the stiffener wire may extend between the proximal and distal ends of the medical device and be secured by each of the end clamps 208.

Moreover, the medical device 200 may have various shapes and configurations for accommodating different target sites. For example, the medical device 200 shown in FIG. 11 may be suitable for treating ASD and VSD. Namely, one end section 202 is sized and configured to overlie or otherwise surround the opening of the ASD or VSD in the right atrium or ventricle as applicable, while the other end section 204 is sized and configured to overlie and/or at least partially radially surround the opening in the left atrium or ventricle as applicable. The central portion 206 is sized and configured to extend through the septal opening, and one or more of the stiffener wires 210, 212 may be configured to also extend through the septal opening and engage the septum. Thus, the stiffener wires 210, 212 are configured to secure the medical device 200 within the ASD or VSD to minimize the amount of contact with the septum while also facilitating fixation of the medical device 200 therein.

Each of the devices discussed above may be used to treat a physiological condition of a patient. Once the appropriate medical device is selected, a catheter or other suitable delivery device may be positioned within a channel in a patient's body to place the distal end of the delivery device adjacent the desired target site, such as immediately adjacent (or even within) the shunt of an abnormal opening in the patient's organ for example.

The delivery device for advancing the medical device through a delivery catheter may take any suitable shape, such as an elongate flexible metal shaft, wire, cable, hypotube, or metal braided polymer tube having a threaded distal end for engagement with a thread formed in the clamp of the medical device. The delivery device can be used to urge the medical device through the lumen of a catheter/sheath for deployment in a channel of a patient's body. When the medical device is deployed out the distal end of the catheter, the delivery device still will retain it. Once the medical device is properly positioned within the shunt of the abnormal opening, the shaft of the delivery device can be rotated about its axis to unscrew the medical device from the delivery device. Regarding the embodiments shown in FIGS. 9, 9A, 10, and 10A, the angular orientation of the medical device may need to be controlled where the medical device is not symmetric. For example, the delivery device may be used to control and position the medical device so that the central portion is properly positioned within the PFO tunnel.

In one embodiment the occluder device, the delivery catheter, and catheter/sheath accommodate a coaxial guidewire that slideably passes through the device, end clamps, and delivery catheter central lumen, and therefore helps guide the delivery device and outer catheter/sheath to the desired location. The guidewire may be delivered independently through the vasculature and across the targeted treatment location or may be extended partially distal to the distal end of the delivery device and catheter/sheath and advanced with the delivery device and catheter/sheath while the guidewire is manipulated to guide the occluder to the desired location. In another embodiment, the catheter/sheath is steerable to assist in placement of the delivery device and occluder. In such an arrangement, either the stiffener wire or guide wire lumen may be positioned non-coaxially within the end clamps, so that the guide wire may be passed therethrough without interference with the stiffener wire. For further discussion regarding a delivery device and methods that may be used to deploy a device according to various aspects of the present invention, see U.S. patent application Ser. No. 11/966,397 to Amplatz et al., which is hereby incorporated in its entirety by reference.

By keeping the medical device attached to the delivery device, the operator can retract the device for repositioning relative to the target site, if it is determined that the device is not properly positioned. A threaded clamp attached to the medical device allows the operator to control the manner in which the medical device is deployed out the distal end of the catheter. When the medical device exits the catheter, it will tend to resiliently return to its preset, expanded shape. When the device springs back into this shape, it may tend to act against the distal end of the catheter effectively urging itself forward beyond the end of the catheter. This spring action could conceivably result in improper positioning of the device if the location of the device within a target site is critical, such as where it is being positioned in a shunt between two vessels. Since the threaded clamp can enable the operator to maintain a hold on the device during deployment, the spring action of the device can be controlled by the operator to ensure proper positioning during deployment.

The medical device can be collapsed into its reduced diameter configuration and inserted into the lumen of the catheter. The collapsed configuration of the device may be of any shape suitable for easy passage through the lumen of a catheter and proper deployment out the distal end of the catheter. For example, the device may have a relatively elongated collapsed configuration wherein the device is stretched along its axis (see e.g., FIG. 5). This collapsed configuration can be achieved simply by stretching the device generally along its axis, e.g., by manually grasping the clamps and pulling them apart, which will tend to collapse the expanded diameter portions of the device inwardly toward the device's axis. In this regard, these devices are not unlike "Chinese handcuffs", which tend to constrict in diameter under axial tension.

If the device is to be used to permanently occlude a target site in the patient's body, one can simply retract the catheter and remove it from the patient's body. This will leave the medical device deployed in the patient's vascular system so that it may occlude the target site in the patient's body. In some circumstances, the medical device may be attached to a delivery system in such a manner as to secure the device to the end of the delivery means. Before removing the catheter in such a system, it may be necessary to detach the medical device from the delivery means before removing the catheter and the delivery means.

Although the device will tend to resiliently return to its initial expanded configuration, i.e., its shape prior to being collapsed for passage through the catheter, it should be understood that it might not always return entirely to that shape. For example, for devices intended to occlude a vessel and placed within the vessel, it may be desirable that the device has a maximum outer diameter in its expanded configuration at least as large as and preferably larger than, the inner diameter of the lumen of the abnormal opening in which it is to be deployed. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat the device therein.

When the device is deployed in a patient, thrombi, protein, and/or other body deposits will tend to collect on the surface of the wires. By having a high wire density and small flow passages between wires as afforded by the one or more layers of fabric, the total surface area of the wires and flow resistance will be increased, increasing the thrombotic activity of the device and permitting it to relatively rapidly occlude the passageway in which it is deployed.

The device may be delivered and properly placed using two dimensional ICE, MRI, transesphogeal echocardiograpy, angiography, and/or Doppler color flow mapping. With the advent of two dimensional ICE, MRI, transesophageal echocardiography, bi-plane angiography, and Doppler color flow mapping, the approximate anatomy of the defect can be visualized. The device that is employed will be based on the approximate size of the vessel or abnormality to be occluded.

The embodiments described above may be employed for treating various vascular abnormalities, such as PDA, VSD, ASD, PFO, PVL, LAA, AVM, or any other similar flow or anatomical abnormality. The occluder devices may have a lower profile, improved retention or clamping force, and improved conformability to adjust to a variety of anatomical variations. With respect to the PFO, for example, the medical device may provide improved clamping force without distorting the PFO flap and may be made of softer materials resulting in a smaller delivery profile, less tissue abrasion, and improved conformability to the PFO.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical device for treating a target site comprising:
 a tubular structure comprising proximal and distal ends and at least one layer of braided material configured to facilitate thrombosis, the tubular structure having a preset, expanded configuration and comprising a first end section at the proximal end and a second end section at the distal end each having a cross-sectional dimension larger than that of an opening of the target site in the preset, expanded configuration, the tubular structure further comprising a central portion extending between the first end section and the second end section, wherein the first end section and the second end section are disposed non-coaxially with respect to one another in the preset, expanded configuration, and wherein the central portion comprises a first portion extending from the first end section, a second portion extending from the second end section, and a third portion extending from the first portion to the second portion, wherein the first and second portions extend substantially perpendicularly with respect to each of the first and second end sections in the preset, expanded configuration, and the third portion extends linearly and substantially parallel to the first and second end sections in the preset, expanded configuration; and
 a single stiffener wire having a preset, expanded configuration, the stiffener wire comprising proximal and distal ends, the proximal end of the stiffener wire affixed to the proximal end of the tubular structure, the stiffener wire configured to extend at least partially through the opening and configured to apply a clamping force on the first end section and the second end section so as to facilitate drawing the first end section and the second end section toward each other and securing at least the first end section over the opening in the preset, expanded configuration, the stiffener wire comprising one or more loops within the tubular structure in the preset, expanded configuration, wherein the one or more loops are disposed within each end section and have a cross-sectional dimension larger than that of the opening of the target site;
 wherein each of the tubular structure and stiffener wire are configured to be constrained from their preset, expanded configurations to a respective reduced configuration for delivery to the target site and to at least partially return to their respective preset, expanded configurations at the target site when unconstrained.

2. The medical device of claim 1, wherein the first end section is disk shaped.

3. The medical device of claim 1, wherein the central portion is configured to extend through a lumen, and wherein the central portion has a cross-sectional dimension at least as large as that of the lumen.

4. The medical device of claim 3, wherein each of the first and second end sections has a cross-sectional dimension that is larger than a cross-sectional dimension of the central portion, and wherein each of the first end section and the second end section is configured to cover a respective opening of the lumen.

5. The medical device of claim 3, wherein the lumen is one of: a) a tunnel of a Patent Foramen *Ovale,* b) a Septal Defect, c) a Patent Ductus Arteriosus, d) a Left Atrial Appendage, or e) an Arterial Venous Malformation.

6. The medical device of claim 1, wherein the stiffener wire is disposed within and between the first end section and the second end section.

7. The medical device of claim 6, wherein one of the first end section and the second end section is configured to cover an opening of a tunnel of a patent foramen ovale in a right atrium, and wherein the other end section is configured to cover an opening of the tunnel in a left atrium.

8. The medical device of claim 1, wherein the at least one layer of braided material comprises a plurality of braided strands comprising at least one material selected from the group consisting of metals, metallic alloys, and polymers.

9. The medical device of claim 1, wherein the tubular structure and stiffener wire comprise a shape memory material.

10. The medical device of claim 1, further comprising a pair of end clamps, wherein each of the proximal and distal ends of the tubular structure is secured with a respective end clamp of the pair of end clamps.

11. The medical device of claim 10, wherein the proximal or distal end of the stiffener wire is secured with one of the end clamps.

12. The medical device of claim 10, wherein the proximal and distal ends of the stiffener wire are secured with respective end clamps of the pair of end clamps.

13. The medical device of claim 1, wherein the stiffener wire comprises a stiffer material than the tubular structure.

14. The medical device of claim 1, wherein the tubular structure and stiffener wire are configured to be elongated to approximately the same length in the reduced configuration.

15. The medical device of claim 1, wherein the stiffener wire is configured to extend through a tunnel of a patent foramen ovale, and wherein the first end section is configured to cover an opening of the tunnel in a right atrium.

16. The medical device of claim 15, wherein the stiffener wire is configured to extend through the tunnel of the patent foramen ovale and at least partially radially surround an opening of the tunnel in a left atrium.

17. The medical device of claim 1, wherein the stiffener wire has a diameter that varies along a length of the stiffener wire.

18. The medical device of claim 1, wherein the expanded configuration of the tubular structure is formed by at least one of: a) a heat treatment of the fabric while in the expanded configuration to preset the expanded configuration; or b) by the preset shape of the stiffener wire exerting force against the tubular structure.

19. The medical device of claim 1, wherein the tubular structure and the stiffener wire comprise different materials.

20. The medical device of claim 1, wherein the at least one layer of braided material comprises a plurality of layers of braided material, and wherein the braided material comprises at least one material selected from the group consisting of metals, metallic alloys, and polymers.

21. The medical device of claim 1, wherein the at least one layer of braided material comprises a plurality of braided strands, and wherein a diameter of the stiffener wire is larger than a diameter of each of the strands.

22. The medical device of claim 1, wherein the tubular structure comprises a plurality of layers of braided material.

23. A method for delivering a medical device to a target site, the method comprising:
providing the medical device according to claim 1;
constraining the medical device in a catheter;
delivering the constrained medical device to the target site; and
deploying the constrained medical device from the catheter such that the medical device at least partially returns to the preset, expanded configuration at the target site and the end section covers an opening of the target site.

24. The method of claim 23, wherein said deploying comprises deploying the medical device such that one of the end sections is configured to cover an opening of a tunnel of a patent foramen ovale in the right atrium, and where the other end section is configured to cover an opening of the tunnel in the left atrium.

25. The method of claim 23, wherein the central portion is configured to extend through a tunnel of a patent foramen ovale, wherein the central portion has a cross-sectional dimension at least as large as that of the tunnel.

26. The method of claim 25, wherein said deploying comprises deploying the medical device such that the central portion extends through and engages the tunnel of the patent foramen ovale.

27. The method of claim 23, wherein said deploying comprises deploying the medical device such that the stiffener wire at least partially radially surrounds the opening in the preset, expanded configuration.

28. The method of claim 23, wherein said deploying comprises deploying the medical device such that the stiffener wire extends through a tunnel of a patent foramen ovale and the end section covers an opening of the tunnel in the right atrium.

29. The method of claim 28, wherein said deploying comprises deploying the medical device such that the stiffener wire extends through the tunnel of the patent foramen ovale and at least partially radially surrounds an opening of the tunnel in the left atrium.

30. The method of claim 28, wherein said deploying comprises controlling and positioning angular orientation of the medical device relative to the tunnel.

31. The method of claim 23, wherein said constraining comprises elongating the tubular structure and stiffener wire to approximately the same length in a reduced configuration.

32. The method of claim 23, wherein said deploying comprises deploying the medical device such that the stiffener wire applies a clamping force to the end sections.

33. A medical device for treating a target site comprising:
a tubular structure having a preset, initial, expanded configuration and comprising proximal and distal ends and at least one layer of braided material configured to facilitate thrombosis, the tubular structure comprising an end section at each of the proximal and distal ends having a cross-sectional dimension larger than that of an opening of the target site, the tubular structure further comprising a central portion extending between the end sections, wherein the central portion comprises a first portion extending from the first end section, a second portion extending from the second end section, and a third portion extending from the first portion to the second portion, wherein the first and second portions extend substantially perpendicularly with respect to each of the first and second end sections in the preset, expanded configuration, and the third portion extends linearly and substantially parallel to the first and second end sections in the preset, initial, expanded configuration; and
a single stiffener wire having a preset, initial, expanded configuration and comprising proximal and distal ends, the proximal end of the stiffener wire affixed to the proximal end of the tubular structure and the distal end of the stiffener wire affixed to the distal end of the tubular structure, the stiffener wire positioned within each of the end sections and the central portion and comprising one or more loops within the tubular structure in the preset, initial, expanded configuration, wherein the one or more loops are disposed within each end section and have a cross-sectional dimension larger than that of the opening of the target site, and wherein the stiffener wire is configured to extend at least partially through the opening and configured to apply a clamping force on the end sections so as to facilitate drawing the end sections toward each other in the preset, initial, expanded configuration,
wherein the end sections of the tubular structure are disposed non-coaxially with respect to one another in the respective preset, initial, expanded configurations, wherein the tubular structure and stiffener wire are configured to be constrained from the respective preset, initial, expanded configurations to respective reduced configurations for delivery to the target site and to at least partially return to the respective preset, initial, expanded configurations at the target site when unconstrained.

34. The medical device of claim 33, wherein one of the end sections is configured to cover an opening of a tunnel of a patent foramen ovale in a right atrium, and wherein the other end section is configured to cover an opening of the tunnel in a left atrium.

35. The medical device of claim 34, wherein the central portion has a cross-sectional dimension at least as large as that of the tunnel.

36. The medical device of claim 33, further comprising a pair of end clamps, wherein each of the proximal and distal ends of the tubular structure is secured with a respective end clamp of the pair of end clamps.

37. The medical device of claim 36, wherein the proximal and distal ends of the stiffener wire are secured with respective end clamps of the pair of end clamps.

38. The medical device of claim 33, wherein the stiffener wire comprises a stiffer material than the tubular structure and is configured to apply a clamping force between the end sections.

39. The medical device of claim 33, wherein the tubular structure and stiffener wire each comprise a shape memory material.

40. The medical device of claim 33, wherein the stiffener wire is further configured to ensure that the end sections are axially offset from one another in the preset, initial, expanded configuration.

41. The medical device of claim 33, wherein the at least one layer of braided material comprises a plurality of layers of braided strands.

42. The medical device of claim 41, wherein at least one layer of the plurality of layers comprises polymer strands.

43. A medical device for treating a target site comprising:
a tubular structure having a preset, initial, expanded configuration and comprising proximal and distal ends and at least one layer of braided material configured to facilitate thrombosis, the tubular structure comprising an end section at the proximal end and an end section at the distal end, each having a cross-sectional dimension larger than that of an opening of the target site, the tubular structure further comprising a central portion extending between the end section at the proximal end and the end section at the distal end, wherein the end section at the proximal end and the end section at the distal end are disposed non-coaxially with respect to one another in the preset, initial, expanded configuration, and wherein the central portion comprises a first portion extending from the first end section, a second portion extending from the second end section, and a third portion extending from the first portion to the second portion, wherein the first and second portions extend substantially perpendicularly with respect to each of the first and second end sections in the preset, expanded configuration and the third portion extends linearly and substantially parallel to the first and second end sections in the preset initial expanded configuration; and
a single stiffener wire having a preset, initial, expanded configuration and comprising proximal and distal ends, the proximal or distal end of the stiffener wire affixed to the proximal or distal end of the tubular structure, the stiffener wire comprising one or more loops in the preset, initial, expanded configuration formed of a stiffer material than the at least one layer of braided material, the one or more loops having a cross-sectional dimension larger than that of the opening of the target site, the stiffener wire configured to extend at least partially through the opening and configured to apply a clamping force on the end sections so as to facilitate drawing the end sections toward each other and securing the end sections over the opening in the preset, initial, expanded configuration,
wherein the tubular structure and the stiffener wire are configured to be constrained from the respective preset, initial, expanded configurations to respective reduced configurations for delivery to the target site and to at least partially return to the respective preset, initial, expanded configurations at the target site when unconstrained.

44. The medical device of claim 43, wherein the end sections are configured to cover an opening of a tunnel of a patent foramen ovale in a right atrium, and wherein the one or more loops of the stiffener wire are configured to at least partially radially surround an opening of the tunnel in a left atrium.

45. The medical device of claim 43, wherein the stiffener wire is at least partially disposed within the tubular structure.

46. The medical device of claim 43, wherein the stiffener wire comprises a plurality of loops.

47. The medical device of claim 43, wherein at least one end section and at least one of the one or more loops of the stiffener wire are disposed non-coaxially with respect to one another in the preset, initial, expanded configuration.

48. The medical device of claim 43, wherein the tubular structure and stiffener wire each comprise a shape memory material.

* * * * *

UNITED STATES PATENT AND TRADEMARK OFFICE
CERTIFICATE OF CORRECTION

PATENT NO. : 10,702,275 B2  
APPLICATION NO. : 12/372854  
DATED : July 7, 2020  
INVENTOR(S) : Adams et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1304 days.

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*